US00PP26340P3

(12) United States Plant Patent
DeGroot

(10) Patent No.: US PP26,340 P3
(45) Date of Patent: Jan. 19, 2016

(54) ***HYPERICUM* PLANT NAMED 'RUIHYH009A'**

(50) Latin Name: *Hypericum×Inodorum*
Varietal Denomination: RUIHYH009A

(71) Applicant: DeRUITER INTELLECTUAL PROPERTY B.V., Amstelveen (NL)

(72) Inventor: Hendrikus C. A. DeGroot, Amstelveen (NL)

(73) Assignee: De Ruiter Intellectual Property B.V., Amstelveen (NL)

( * ) Notice: Subject to any disclaimer, the term of this patent is extended or adjusted under 35 U.S.C. 154(b) by 122 days.

(21) Appl. No.: 13/998,420

(22) Filed: Oct. 30, 2013

(65) Prior Publication Data

US 2015/0121595 P1 Apr. 30, 2015

(51) Int. Cl.
*A01H 5/00* (2006.01)

(52) U.S. Cl.
USPC ..... Plt./442

(58) Field of Classification Search
USPC ..... Plt./442
See application file for complete search history.

*Primary Examiner* — Keith Robinson
(74) *Attorney, Agent, or Firm* — Barbara Campbell; Cochran Freund & Young LLC

(57) ABSTRACT

A new *Hypericum* plant particularly distinguished by red berries, bright green leaves, and an upright, dense, and bushy plant habit, is disclosed.

2 Drawing Sheets

Genus and species: *Hypericum×Inodorum.*
Variety denomination: 'RUIHYH009A'.

BACKGROUND OF THE NEW PLANT

The present invention comprises a new and distinct variety of *Hypericum,* botanically known as *Hypericum×Inodorum,* and hereinafter referred to by the variety name 'RUIHYH009A'. 'RUIHYH009A' originated from a cross conducted in June 2007 in Hazerswoude, The Netherlands between the proprietary female *Hypericum* variety 'Hp-04-0126-003' (unpatented), and pollen from a mixture of un-named male *Hypericum* varieties.

The seeds from the cross were sown and plants were grown outdoors for evaluation. An individual plant designated 'RUIHYH009A' was selected in October 2010. 'RUIHYH009A' was first vegetatively propagated in May 2010 in Hazerswoude, The Netherlands by softwood cuttings. 'RUIHYH009A' was found to reproduce true to type in successive generations of asexual propagation via softwood cuttings.

'RUIHYH009A' has not been made publicly available or sold more than one year prior to the filing date of this application.

SUMMARY

The following are the most outstanding and distinguishing characteristics of this new variety when grown under normal horticultural practices in Hazerswoude, The Netherlands.

1. Red berries;
2. Bright green leaves; and
3. An upright, dense, and bushy plant habit.

DESCRIPTION OF THE PHOTOGRAPHS

This new *Hypericum* plant is illustrated by the accompanying photographs which show the plant's overall plant habit including form, foliage, and berries. The photograph is of a one-year-old plant grown in outdoors in Hazerswoude, The Netherlands in September 2010. The colors shown are as true as can be reasonably obtained by conventional photographic procedures.

DESCRIPTION OF THE NEW VARIETY

Figure 1:
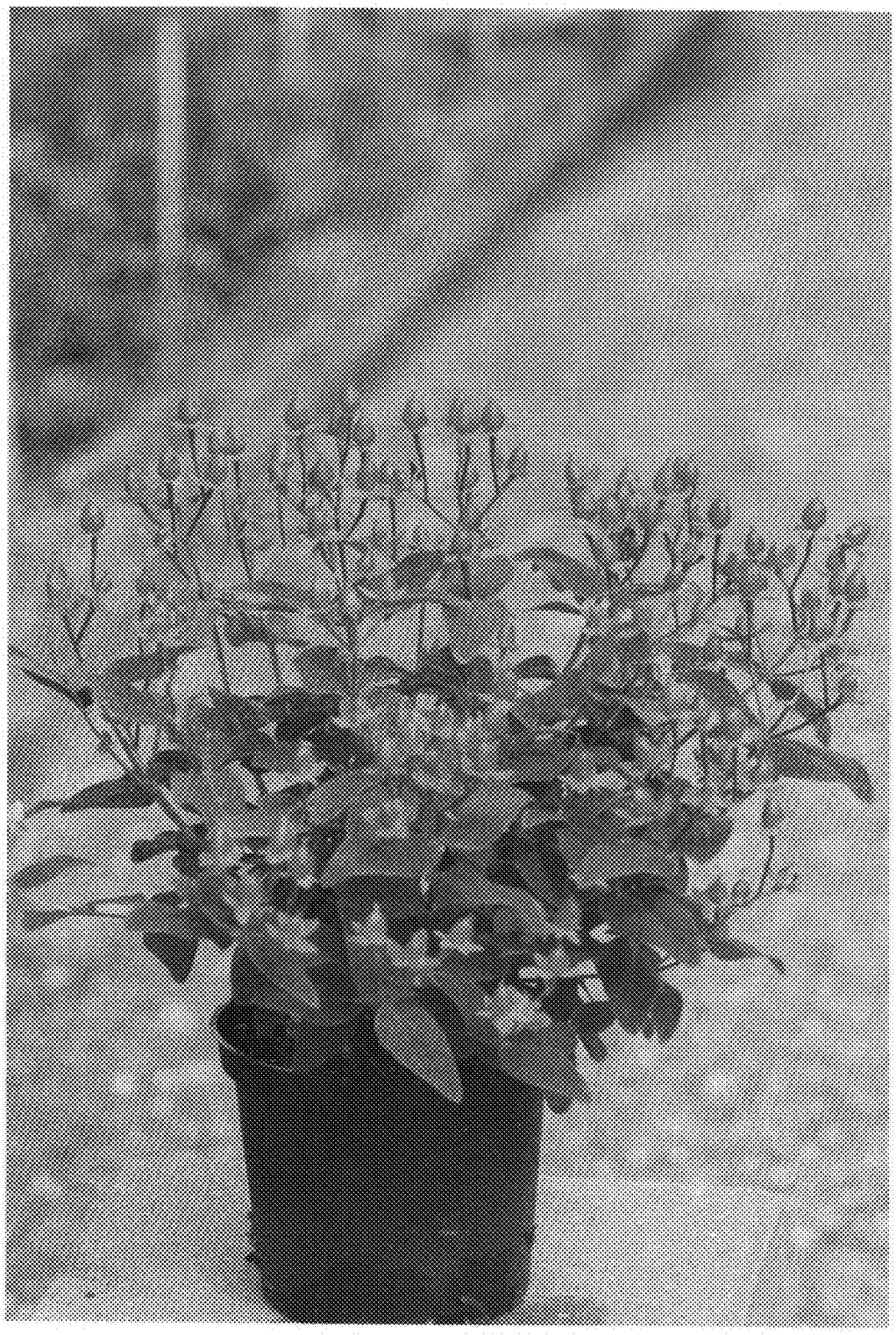
FIG. 1 shows the overall plant habit in a pot.
Figure 2:
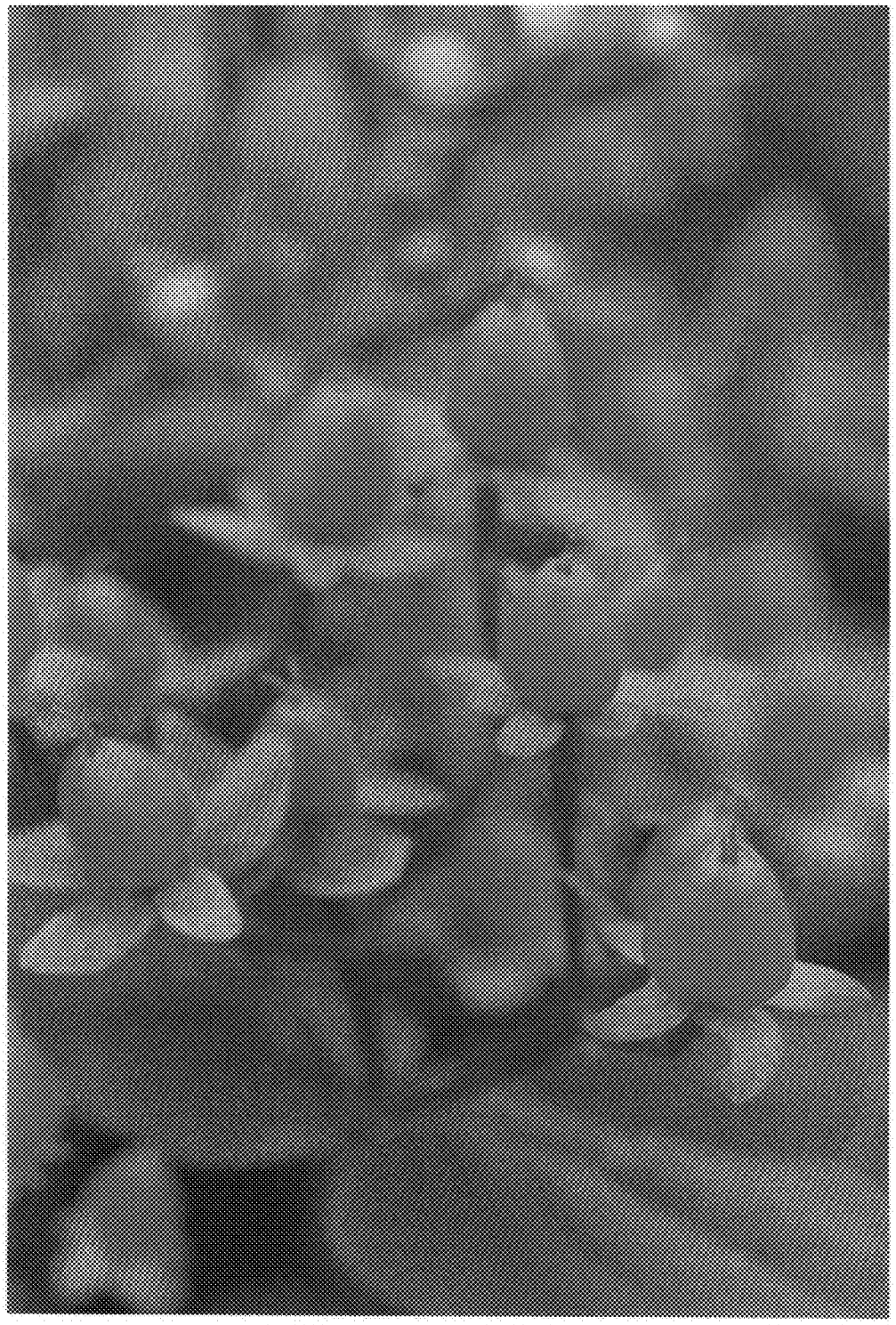
FIG. 2 shows a close-up of the foliage and berries.

The following detailed descriptions set forth the distinctive characteristics of 'RUIHYH009A'. The data which define these characteristics were collected from one-year-old plants grown outdoors in Amstelveen, The Netherlands in September 2013. Color references are to The R.H.S. Colour Chart of The Royal Horticultural Society of London (R.H.S.), 1995.

Classification:

*Family.*—Hypericeae.
*Botanical.*—*Hypericum×Inodorum.*
*Designation.*—'RUIHYH009A'.
*Parentage.*—Female parent: The proprietary female *Hypericum* variety 'Hp-04-0126-003' (unpatented). Male parent: A mixture of pollen from un-named *Hypericum* varieties.

Plant:

*Form.*—Upright.
*Habit.*—Dense, bushy.
*Height* (*measured from the top of the soil*).—24.0 cm.
*Width* (*horizontal plant diameter*).—30.0 cm.
*Time to produce a finished plant.*—8 months.
*Outdoor plant performance.*—For use in pots.
*Time to initiate and develop roots.*—14 to 21 days.
*Root description.*—Fibrous, well-branched; when young, are white, but older roots are RHS 165A (Brown).
*Propagation type.*—Softwood cutting.
*Growing season.*—Flowers in the summer and berries develop in September.

Stems:
*Quantity per plant.*—Average is 20.
*Length.*—About 17.0 cm.
*Internode length.*—3.0 cm.
*Diameter (from midpoint).*—About 3.0 mm.
*Color.*—RHS 173A.
*Texture.*—Smooth.
*Anthocyanin.*—Present, RHS 173A.
*Strength.*—Strong.

Leaves:
*Arrangement.*—Decussate.
*Length.*—5.0 cm.
*Width.*—2.5 cm.
*Shape.*—Oval to lanceolate.
*Apex.*—Acute.
*Base.*—Cordate.
*Margin.*—Entire.
*Color, immature.*—Upper surface: RHS 138A. Lower surface: RHS 138C.
*Color, mature.*—Upper surface: RHS 137A. Lower surface: RHS 138B.
*Texture (both upper and lower surfaces).*—Smooth.
*Venation type.*—Pinnate.
*Venation color.*—Upper surface: RHS 137A. Lower surface: RHS 138B.
*Petiole.*—Absent.

Inflorescence:
*Type.*—Cyme, compound, composed of approximately 7 cymes.
*Height.*—6.0 cm.
*Width.*—4.5 cm.
*Flowering season.*—Summer.
*Fragrance.*—Absent.
*Peduncle.*—Length: 10.0 mm. Diameter: 1.0 mm. Color: RHS 46C. Strength: Weak. Texture: Smooth.

Bud:
*Color.*—RHS 17C.
*Shape.*—Round.
*Height.*—0.8 cm.
*Diameter.*—0.7 cm.
*Texture.*—Smooth.

Flower:
*Depth.*—1.0 cm.
*Diameter.*—2.3 cm.
*Quantity per inflorescence.*—6.
*Petals.*—Arrangement and quantity of petals per flower: Single, composed of 5 petals per flower. Length: 0.8 cm. Width: 0.6 cm. Shape: Obovate. Apex: Rounded. Base: Cuneate. Margin: Entire. Texture (both upper and lower surfaces): Smooth. Color (both immature and mature): Upper surface: RHS 13A. Lower surface: RHS 13B.

Calyx:
*Arrangement and quantity of sepals per flower.*—5.
*Shape.*—Flat.
*Sepals.*—Length: 1.0 cm. Width: 0.8 cm. Shape: Ovate. Apex: Acute. Base: Cordate. Margin: Entire. Texture (both upper and lower surfaces): Smooth. Color: Upper surface: RHS 138A. Lower surface: RHS 139D.

Pedicel:
*Length.*—2.0 cm.
*Diameter.*—0.15 cm.
*Color.*—RHS 173A.
*Texture.*—Smooth.

Reproductive organs:
*Stamens.*—Quantity per flower: About 45. Filament: Length: 0.7 cm. Width: 0.2 mm. Color: RHS 11A. Anther: Length: 0.08 cm. Width: 0.5 mm. Color: RHS 15A. Pollen amount: Moderate. Pollen color: RHS 13B.
*Pistil.*—Quantity per flower: 3. Length: 0.4 cm. Width: 5.0 mm. Stigma: Shape: Globular. Color: RHS 183A. Quantity of stigma per pistil: 3. Style: Length: 0.4 cm. Color: RHS 153D. Ovary: Color: RHS 37A. Length: 7.0 mm. Width: 5.0 mm.

Fruit and seed set: Berries observed; 6 berries per inflorescence, berries are smooth and matte in glossiness, berries are ovate in shape, 1.4 cm in length, 1.0 cm in width, and RHS 45B.

Disease and pest/insect resistance: No disease and pest/insect resistance observed or tested.

COMPARISON WITH PARENTAL LINE AND KNOWN VARIETY

'RUIHYH009A' is a distinct variety of *Hypericum* and is distinguished from its female parent as described in Table 1.

TABLE 1

Comparison with Parental Line

| Characteristic | 'RUIHYH009A' | Female Parent 'Hp-04-0126-003' |
|---|---|---|
| Berry color | Red | Green |

When 'RUIHYH009A' is compared to the commercial variety 'Seibig' (U.S. Plant Pat. No. 20,668), the following differences are described in Table 2.

TABLE 2

Comparison with Similar Variety

| Characteristic | 'RUIHYH009A' | 'Seibig' |
|---|---|---|
| Plant height | 24.0 cm | 70.0 cm |
| Plant width | 30.0 cm | 50.0 cm to 60.0 cm |

I claim:

1. A new and distinct variety of *Hypericum* plant designated 'RUIHYH009A' as illustrated and described herein.

* * * * *